(12) United States Patent
Cunningham

(10) Patent No.: US 10,445,390 B2
(45) Date of Patent: Oct. 15, 2019

(54) COORDINATION OF DENTAL IMPLANT INFORMATION

(71) Applicant: Carol A. Cunningham, Decatur, IL (US)

(72) Inventor: Carol A. Cunningham, Decatur, IL (US)

( * ) Notice: Subject to any disclaimer, the term of this patent is extended or adjusted under 35 U.S.C. 154(b) by 826 days.

(21) Appl. No.: 14/826,917

(22) Filed: Aug. 14, 2015

(65) Prior Publication Data

US 2017/0046486 A1   Feb. 16, 2017

(51) Int. Cl.
*G06F 16/955* (2019.01)
*G06F 3/0482* (2013.01)
*G06F 3/0484* (2013.01)
*G16H 10/60* (2018.01)

(52) U.S. Cl.
CPC .......... *G06F 16/955* (2019.01); *G06F 3/0482* (2013.01); *G06F 3/04842* (2013.01); *G16H 10/60* (2018.01)

(58) Field of Classification Search
CPC .... G06F 19/32; G06F 2/0482; G06F 3/04842; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00

See application file for complete search history.

(56) References Cited

U.S. PATENT DOCUMENTS

| 2009/0155744 A1 | 6/2009 | Jandali | |
| 2010/0161345 A1* | 6/2010 | Cain | G06F 19/328 705/2 |
| 2012/0189182 A1* | 7/2012 | Liang | A61C 19/00 382/131 |

(Continued)

OTHER PUBLICATIONS

"Dental Implant Failure Rates and associated factors." Moy, PK; Medina, D; Shetty V; Aghaloo TL. Int J Oral Maxillofac Implants. Jul.-Aug. 2005; 20(4):569-77 (Year: 2005).*

(Continued)

*Primary Examiner* — Linh Giang Le
*Assistant Examiner* — Lin Giang Michelle Le
(74) *Attorney, Agent, or Firm* — McDonnell Boehnen Hulbert & Berghoff LLP

(57) ABSTRACT

A dental patient interface on a computing device may display data related to a dental patient. The data may include identifying information for the dental patient, dental appointment scheduling information for the dental patient, and dental history information regarding a plurality of teeth of the dental patient. The dental patient interface may receive a selection of a particular tooth of the plurality of teeth. Possibly in response to the selection of the particular tooth, the dental patient interface may display a dental history of the particular tooth, the dental history including dental implant information. The dental implant information may identify dental implant components forming the particular tooth or prosthesis by implant manufacturer and/or part number.

20 Claims, 14 Drawing Sheets

(56) References Cited

U.S. PATENT DOCUMENTS

2013/0346109 A1\* 12/2013 Gunn .................... G06F 19/322
    705/3
2014/0229190 A1   8/2014 Royal et al.
2015/0019252 A1\* 1/2015 Dawson .................. A61C 8/00
    705/3

OTHER PUBLICATIONS

International Search Report dated Nov. 10, 2016 for International Application No. PCT/US2016/039789 filed Jun. 28, 2016.
Transmittal of Written Opinion dated Nov. 10, 2016 for International Application No. PCT/US2016/039789 filed Jun. 28, 2016.
ADA, PatentSmart Patient Education Center, Tooth Replacement Options, 2013, 6 pages.
Dear Doctor, "Dental Implants, Your Best Option for Replacing Missing Teeth," http://www.deardoctor.com/dental-implants, last accessed Jul. 27, 2015, 4 pages.

\* cited by examiner

FIG. 6A

DASHBOARD VIEW

| | July 15 | | | | | |
|---|---|---|---|---|---|---|
| S | M | T | W | T | F | S |
| | | | 1 | 2 | 3 | 4 |
| 5 | 6 | 7 | 8 | 9 | 10 | 11 |
| 12 | 13 | 14 | 15 | 16 | 17 | 18 |
| 19 | 20 | 21 | 22 | 23 | 24 | 25 |
| 26 | 27 | 28 | 29 | 30 | 31 | |

DENTIST: Jane A. Doe

SEARCH 🔍 612

| PATIENT NAME | LATEST EVENT | UPCOMING EVENT(S) |
|---|---|---|
| Alice Smith | 6/27/15 Scheduled for dental implant surgery | 7/8/15 Dental implant surgery with Dr. Thomas |
| Robert Jones | 6/29/15 Dental implant surgery conducted by Dr. Roberts | 8/15/15 Appointment – follow up from surgery |
| Cathy Benton | 6/25/15 Dental implants ordered from Company A | 7/7/15 Abutments scheduled to arrive |

• • •

DENTAL IMPLANT EFFICACY VIEW

Results
650

| SORT BY: | Dental Implant Part No. | Manufacturer | Failure Rate |
|---|---|---|---|
| Part type: dental implant | VZW100 | Company A | 10% |
| Manufacturer: Company A | VZW250 | Company A | 6% |
| Dental Specialist: all | VZW300 | Company A | 2% |
| Date of surgery: 1/1/2000 - present | VZW350 | Company A | 4% |

FIG. 6C

COORDINATION OF DENTAL IMPLANT INFORMATION

BACKGROUND

In spite of improvements in dental care, many individuals experience tooth loss. This loss may be due to tooth decay, gum disease (e.g., gingivitis), or injury. It is desirable to replace a lost tooth with an artificial tooth as soon as possible. This will prevent remaining teeth from drifting out of line and possibly causing jaw problems. Also, teeth that are out of line are harder to clean and this may exacerbate any decay and/or gum disease thereof.

For many years, the treatment options for people with missing teeth were bridges and dentures. But, a bridge often requires altering nearby teeth for support. Dentures may slip in the dental patient's mouth, impeding chewing and speech, and exhibit significant inconvenience due to needing to be removed for cleaning.

Today, dental implants are available. Dental implants are replacement tooth roots that provide a foundation for permanent or removable replacement teeth (e.g., crowns or prostheses). The replacement teeth can be made to match the dental patient's natural teeth. Dental implants do not suffer from the disadvantages of bridges and dentures, and typically have a very high success rate.

Nonetheless, placement of dental implants may involve coordination between a general dentist and a dental specialist with regard to the dental patient scheduling and the components used for the dental implants. Currently this process is painstaking and error-prone. Further, dental patient medical records regarding past dental implant consultations and surgeries, as well as dental implant restorative work and the parts used in these procedures, are often difficult to obtain from other dental professionals, difficult to interpret, or even non-existent or unavailable, making it problematic to repair existing dental implants.

SUMMARY

In a first example embodiment, a dental patient interface on a computing device may display data related to a dental patient. The data may include identifying information for the dental patient, dental appointment scheduling information for the dental patient, and dental history information regarding a plurality of teeth of the dental patient. The dental patient interface may receive a selection of a particular tooth of the plurality of teeth. Possibly in response to the selection of the particular tooth, the dental patient interface may display a dental history of the particular tooth, the dental history including dental implant information. The dental implant information may identify dental implant components utilized to restore the particular tooth by manufacturer and/or part number.

A second example embodiment may involve displaying, by a computing device, one of a dental patient interface, a dental patient list interface, and a dental implant component interface. The dental patient interface may include data related to a dental patient. The data may include identifying information for the dental patient, dental appointment scheduling information for the dental patient, and dental history information regarding a plurality of teeth of the dental patient. The dental patient list interface may include data related to a plurality of dental patients. At least some of the dental patients have had dental implant surgery. The dental implant component interface may include data related to one or more dental implant components for dental implants. The one or more dental implant components may each be associated with respective manufacturers, part numbers, and/or failure rates. The second example embodiment may also involve selecting, by way a control on the displayed interface, another of the dental patient interface, the dental patient list interface, or the dental implant component interface. The second example embodiment may further involve displaying, by the computing device, the selected interface.

In a third example embodiment, an article of manufacture may include a non-transitory computer-readable medium, having stored thereon program instructions that, upon execution by a computing device, cause the computing device to perform operations in accordance with the first and/or second example embodiments.

In a fourth example embodiment, a computing device may include at least one processor, as well as data storage and program instructions. The program instructions may be stored in the data storage, and upon execution by the at least one processor, cause the computing device to perform operations in accordance with the first and/or second example embodiments.

In a fifth example embodiment, a system may include various means for carrying out each of the operations of the first and/or second example embodiments.

These as well as other embodiments, aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

FIG. 6A depicts a dashboard view of a dental patient database, according to an example embodiment.

FIG. 6C depicts a dental implant efficacy view of a dental patient database, according to an example embodiment.

DETAILED DESCRIPTION

Figure 1:
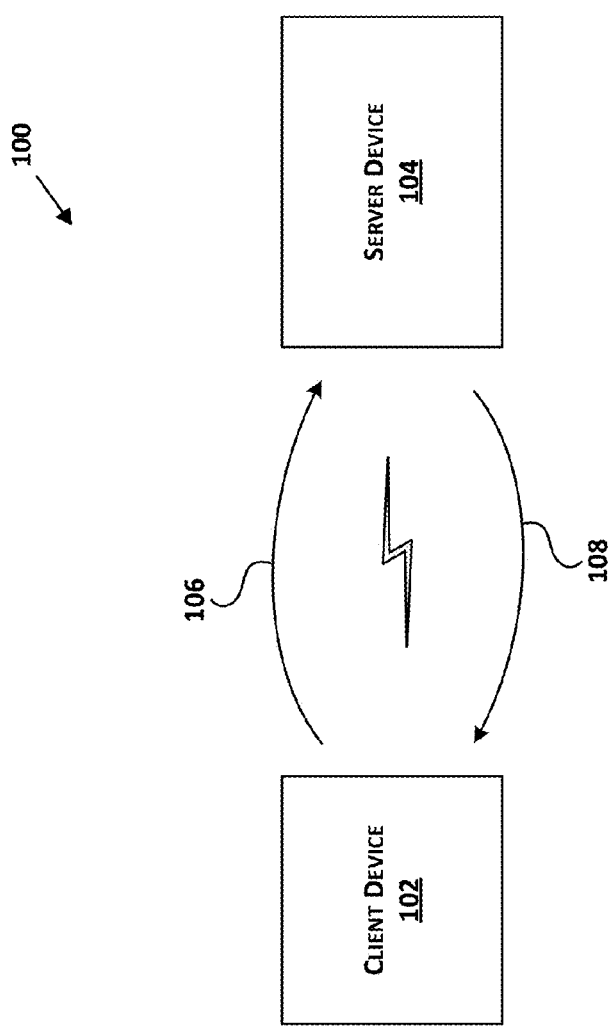
FIG. 1 is a high-level depiction of a client-server computing system, according to an example embodiment.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

1. OVERVIEW

Dental implants are artificial tooth replacements that involve a crown or prosthesis being placed over a post that is surgically fixed into a dental patient's jaw. Dental implants have distinct advantages over bridges and dentures. Bridges require reduction of the adjacent teeth to allow a tooth to be replaced, are difficult to clean, can be subject to decay if not properly cleaned, and can fail due to bone loss. Dentures can be uncomfortable, can result in continual bone loss over time, and require ongoing replacement maintenance.

Typically, obtaining a dental implant involves the dental patient first visiting a general dentist, who recommends the dental implant and refers the dental patient to a dental specialist (e.g., an oral surgeon, periodontist, endodontist, prosthodontist, orthodontist, or another type of dental professional). In some cases, the general dentist may also perform the functions of a dental specialist, and place dental implants in dental patients. If this is the case, a separate dental specialist might not be involved in the procedure.

Regardless, the general dentist may also take an impression of the dental patient's mouth for a surgical guide that can be used by the dental specialist. After consultation with the dental specialist, a dental patient who elects dental implant surgery schedules that surgery with the dental specialist. During surgery, the dental specialist may extract any residual parts of the tooth to be replaced, and place the dental implant (e.g., a small post made of titanium or some other metal) into the bone socket of the extracted tooth or into the jaw.

As the dental patient's jawbone heals, it grows around the dental implant, anchoring the dental implant securely in the jaw. In some cases, the dental patient may elect to have an immediate load procedure where one or more temporary artificial teeth are placed in the dental patient within approximate 48 hours of surgery. A drawback to this approach is that the dental patient may be limited to a soft diet for several weeks or months, and the likelihood of dental implant failure increases. Nonetheless, the embodiments herein include immediate load procedures as an option.

Once the healing is substantially complete (which may take 4-16 weeks), the dental patient may return to the general dentist, who places an abutment on the dental implant. The abutment is a connector that attaches the dental implant to the replacement tooth or prosthesis. The replacement tooth, in turn, may be a crown that is designed to resemble the dental patient's natural teeth. For example, the general dentist may take impression of the dental patient's teeth, and create a model of the dental patient's bite. The crown may be based on this model, so that the crown looks natural in the dental patient's mouth, and completes the dental patient's bite. The crown may even be colored to match the dental patient's natural teeth. Because the dental implant is secured within the jawbone, the replacement tooth looks, feels, and functions just like a natural tooth. See FIGS. 5A and 5B for examples of dental implant components.

At least three distinct, but overlapping, challenges are presented by this process and dental implants in general. First, a significant amount of coordination takes place between the general dentist and the dental specialist, as they hand the dental patient off to one another while coordinating appointments for the dental patient between their offices. Further, in order for the dental patient to be ready for dental implant surgery, a dental professional may need certain images such as cone beam computed tomography scans. Various types of components, such as the surgical guides, scan guides, dental implants, healing abutments, bone graft material, bio-membranes, temporary crowns, screws, and temporary dentures may also be obtained prior to surgery. Currently, the general dentist and dental specialist have no systematic way of tracking their respective appointments, and the dependencies of these appointments on the availability of specific types of dental implant components. As a result, appointments can be erroneously scheduled to occur before the dental patient or the dental implant components are ready. While dental patient scheduling is often computerized in each professional's office, there is presently no way to coordinate this scheduling with other offices, dental labs, and/or implant manufacturers.

Second, there is a wide variety of dental implant components that can be used with dental implants. Some of these dental implant components are proprietary, in that an implant manufacturer's dental implant must be used with specific types of screws or abutments. In some cases, specific dental implant components require specific types of tools. Thus, the general dentist or dental specialist may seek to ensure that the proper parts and tools are on hand for surgery, tooth restoration, and maintenance appointments. Moreover, for dental patients who have had dental implants placed in the past, this information can be lost. Particularly, if the dental patient moves around within a country or internationally, dental patient records may be lost or are unavailable to a new general dentist or dental specialist. Therefore, when either of these professionals attempt to make adjustments or repairs to a dental implant, abutment, crown, or dental implant prosthesis, they may not know what replacement dental implant components to order, or even what tools to use. While computerized records of some of this information may exist in each professional's office, the information cannot be easily shared with other offices.

Third, until now, general dentists, dental specialists, dental labs, and implant manufacturers have had no way to consistently and reliably track the efficacy of particular dental implant components and procedures. In some cases, dental implants fail, perhaps due to improper placement, loss of bone support, traumatic occlusion (e.g., teeth grinding), or infection. To the extent that one or more of these issues may be correlated to a particular type of dental implant or dental implant procedure, such information may be valuable in determining specific dental implant components and dental implant techniques that should be used in the future.

In order to overcome these problems, embodiments herein provide methods, devices, and systems for an interactive, database-driven, computer-mediated application (e.g., a web site or another type of application such as a smartphone "app") that facilitates the coordinated scheduling of dental implant procedures between dental patients, general dentists, dental specialists, dental labs, and/or implant manufacturers. Thus, a general dentist, for example, can use the application to determine the status of a dental patient that has been referred to a dental specialist for a dental implant consultation. The general dentist may be able to determine, from the information presented, whether the dental patient has elected oral surgery, when that surgery is scheduled, whether all appropriate dental implant components have been ordered and are on hand with the dental specialist, and when the dental patient can be scheduled for a follow-up appointment with the general dentist, among other possibilities. This allows the general dentist to schedule dental patient appointments earlier, and to know when scheduled appointments are at risk due to dental implant components not being available, dental prostheses not being completed by the dental lab, or the unavailability of the general dentist to examine the dental patient after surgery.

Further, by retaining information regarding the dental implant components and procedures used for each replacement tooth of a dental patient, this information can be used by other general dentists or dental specialists in the future. For instance, suppose that a dental patient living in California receives a dental implant, then ten years later moves to New York, and the general dentist and dental specialist who provided the dental implant both retired in the mean time. The dental patient can now visit any local general dentist or dental specialist, who can then use the application to determine when the dental implant was inserted, and what dental implant components and procedures were used. Thus, proper maintenance of the dental implant can be achieved and the dental patient can be provided continuity of care.

Moreover, with a large enough database of dental patients and dental implants available to the application, the efficacy of dental implants and dental implant techniques can be tracked. Through this data, general dentists, dental specialists, and/or implant manufacturers can determine, for instance, that a certain type of dental implant component is associated with a failure rate that is twice that of the average failure rate across all types of dental implant components. These parties can then either avoid use of this type of dental implant component in the future, or the implant manufacturers can attempt to make improvements to the dental implant component so that its reliability is increased.

In some cases, the application might not be entirely web-based, and may instead be a standalone application or smartphone app. For instance, the user might download a smartphone app that allows the interactions described herein. Also, scanning devices and/or image capture devices (e.g., cameras) might be used to allow quick and accurate entry of dental implant part information into a dental patient's entry in the database. For instance, rather than undertaking an error-prone manual entry procedure, identifying information (e.g., part numbers) for each dental implant component placed in a dental patient may be scanned or captured into a computing device, and then uploaded to the database. In this way, this identifying information can become part of the dental patient's permanent dental history. Thus, in the future, the same or different dental professionals may be able to access this information to determine how to properly treat the dental patient.

Regardless of how they may be implemented, the embodiments herein may make use of one or more computing devices. These computing devices may include, for example, a client device under the control of a user, and a server device that interacts with the client device. Such devices are described in the following section.

2. EXAMPLE COMPUTING DEVICES AND CLOUD-BASED COMPUTING ENVIRONMENTS

FIG. 1 illustrates an example communication system 100 for carrying out one or more of the embodiments described herein. Communication system 100 may include computing devices. Herein, a "computing device" may refer to either a client device, a server device (e.g., a stand-alone server computer or networked cluster of server equipment), or some other type of computational platform.

Client device 102 may be any type of device including a personal computer, laptop computer, a wearable computing device, a wireless computing device, a head-mountable computing device, a mobile telephone, or tablet computing device, etc., that is configured to transmit data 106 to and/or receive data 108 from a server device 104 in accordance with the embodiments described herein. For example, in FIG. 1, client device 102 may communicate with server device 104 via one or more wireline or wireless interfaces. In some cases, client device 102 and server device 104 may communicate with one another via a local-area network. Alternatively, client device 102 and server device 104 may each reside within a different network, and may communicate via a wide-area network, such as the Internet.

Client device 102 may include a user interface, a communication interface, a main processor, and data storage (e.g., memory). The data storage may contain instructions executable by the main processor for carrying out one or more operations relating to the data sent to, or received from, server device 104. The user interface of client device 102 may include buttons, a touchscreen, a microphone, scanner, and/or any other elements for receiving inputs, as well as a speaker, one or more displays, and/or any other elements for communicating outputs.

Server device 104 may be any entity or computing device arranged to carry out the server operations described herein. Further, server device 104 may be configured to send data 108 to and/or receive data 106 from the client device 102.

Data 106 and data 108 may take various forms. For example, data 106 and 108 may represent packets transmitted by client device 102 or server device 104, respectively, as part of one or more communication sessions. Such a communication session may include packets transmitted on a signaling plane (e.g., session setup, management, and teardown messages), and/or packets transmitted on a media plane (e.g., text, graphics, audio, and/or video data).

Regardless of the exact architecture, the operations of client device 102, server device 104, as well as any other operation associated with the architecture of FIG. 1, can be carried out by one or more computing devices. These computing devices may be organized in a standalone fashion, in cloud-based (networked) computing environments, or in other arrangements.

Figure 2:
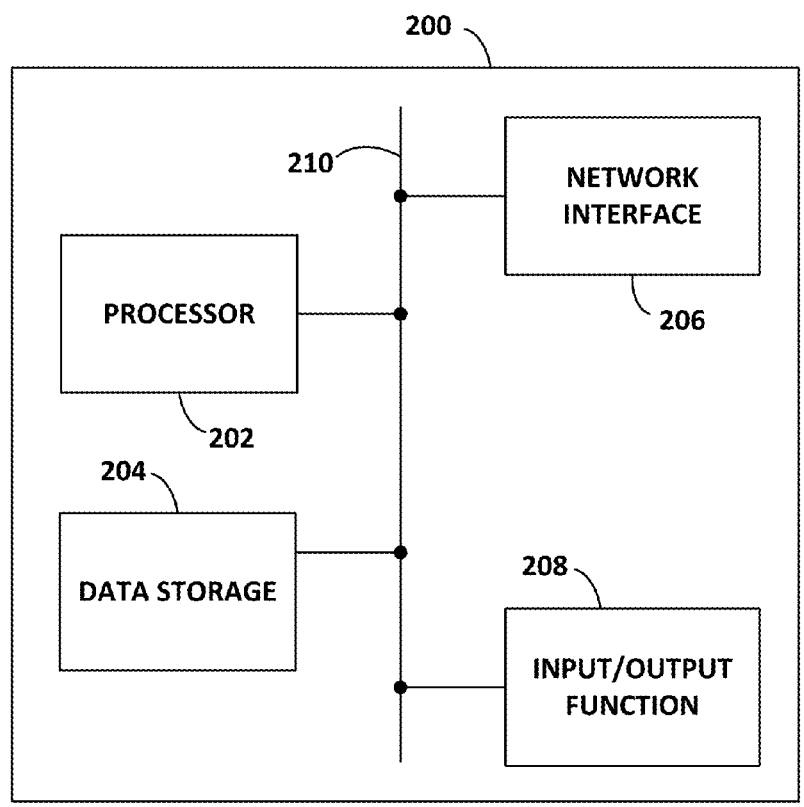
FIG. 2 illustrates a schematic drawing of a computing device, according to an example embodiment.

FIG. 2 is a simplified block diagram exemplifying a computing device 200, illustrating some of the functional components that could be included in a computing device arranged to operate in accordance with the embodiments herein. Example computing device 200 could be a client device, a server device, or some other type of computational platform. For purposes of simplicity, this specification may equate computing device 200 to a server from time to time. Nonetheless, the description of computing device 200 could apply to any component used for the purposes described herein.

In this example, computing device 200 includes a processor 202, a data storage 204, a network interface 206, and an input/output function 208, all of which may be coupled by a system bus 210 or a similar mechanism. Processor 202 can include one or more CPUs, such as one or more general purpose processors and/or one or more dedicated processors (e.g., application specific integrated circuits (ASICs), digital signal processors (DSPs), network processors, etc.).

Data storage 204, in turn, may comprise volatile and/or non-volatile data storage and can be integrated in whole or in part with processor 202. Data storage 204 can hold program instructions, executable by processor 202, and data that may be manipulated by these instructions to carry out the various methods, processes, or operations described herein. Alternatively, these methods, processes, or operations can be defined by hardware, firmware, and/or any combination of hardware, firmware and software. By way of example, the data in data storage 204 may contain program instructions, perhaps stored on a non-transitory, computer-readable medium, executable by processor 202 to carry out any of the methods, processes, or operations disclosed in this specification or the accompanying drawings.

Network interface 206 may take the form of a wireline connection, such as an Ethernet, Token Ring, or T-carrier connection. Network interface 206 may also take the form of a wireless connection, such as IEEE 802.11 (Wifi), BLUETOOTH®, or a wide-area wireless connection. However, other forms of physical layer connections and other types of standard or proprietary communication protocols may be used over network interface 206. Furthermore, network interface 206 may comprise multiple physical interfaces.

Input/output function 208 may facilitate user interaction with example computing device 200. Input/output function 208 may comprise multiple types of input devices, such as a keyboard, a mouse, a touch screen, and so on. Similarly, input/output function 208 may comprise multiple types of output devices, such as a screen, monitor, printer, or one or more light emitting diodes (LEDs). Additionally or alternatively, example computing device 200 may support remote access from another device, via network interface 206 or via another interface (not shown), such as a universal serial bus (USB) or high-definition multimedia interface (HDMI) port.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

Figure 3:
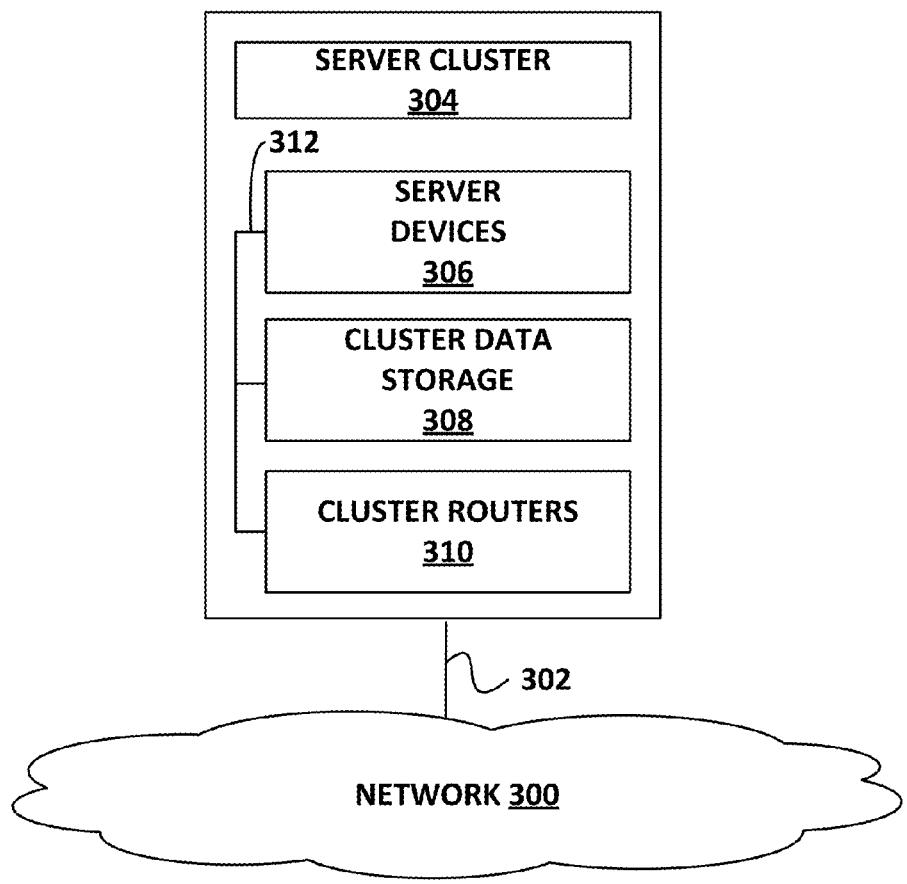
FIG. 3 illustrates a schematic drawing of a networked server cluster, according to an example embodiment.

FIG. 3 depicts a cloud-based server cluster 304 in accordance with an example embodiment. In FIG. 3, functions of a server device, such as server device 104 (as exemplified by computing device 200) may be distributed between server devices 306, cluster data storage 308, and cluster routers 310, all of which may be connected by local cluster network 312. The number of server devices, cluster data storages, and cluster routers in server cluster 304 may depend on the computing task(s) and/or applications assigned to server cluster 304.

For example, server devices 306 can be configured to perform various computing tasks of computing device 200. Thus, computing tasks can be distributed among one or more of server devices 306. To the extent that these computing tasks can be performed in parallel, such a distribution of tasks may reduce the total time to complete these tasks and return a result. For purposes of simplicity, both server cluster 304 and individual server devices 306 may be referred to as "a server device." This nomenclature should be understood to imply that one or more distinct server devices, data storage devices, and cluster routers may be involved in server device operations.

Cluster data storage 308 may be data storage arrays that include disk array controllers configured to manage read and write access to groups of hard disk drives. The disk array controllers, alone or in conjunction with server devices 306, may also be configured to manage backup or redundant copies of the data stored in cluster data storage 308 to protect against disk drive failures or other types of failures that prevent one or more of server devices 306 from accessing units of cluster data storage 308.

Cluster routers 310 may include networking equipment configured to provide internal and external communications for the server clusters. For example, cluster routers 310 may include one or more packet-switching and/or routing devices configured to provide (i) network communications between server devices 306 and cluster data storage 308 via cluster network 312, and/or (ii) network communications between the server cluster 304 and other devices via communication link 302 to network 300.

Additionally, the configuration of cluster routers 310 can be based at least in part on the data communication requirements of server devices 306 and cluster data storage 308, the latency and throughput of the local cluster networks 312, the latency, throughput, and cost of communication link 302, and/or other factors that may contribute to the cost, speed, fault-tolerance, resiliency, efficiency and/or other design goals of the system architecture.

As a possible example, cluster data storage 308 may include any form of database, such as a structured query language (SQL) database. Various types of data structures may store the information in such a database, including but not limited to tables, arrays, lists, trees, and tuples. Furthermore, any databases in cluster data storage 308 may be monolithic or distributed across multiple physical devices.

Server devices 306 may be configured to transmit data to and receive data from cluster data storage 308. This transmission and retrieval may take the form of SQL queries, and the output of such queries, respectively. Additional text, images, video, and/or audio may be included as well. Furthermore, server devices 306 may organize the received data into web page representations. Such a representation may take the form of a markup language, such as the hypertext markup language (HTML), the extensible markup language (XML), or some other standardized or proprietary format. Moreover, server devices 306 may have the capability of executing various types of computerized scripting languages, such as but not limited to Perl, Python, PHP Hypertext Preprocessor (PHP), Active Server Pages (ASP), Javascript, and so on. Computer program code written in these languages may facilitate the providing of web pages to client devices, as well as client device interaction with the web pages.

3. EXAMPLE HIGH LEVEL ARCHITECTURE

Figure 4:
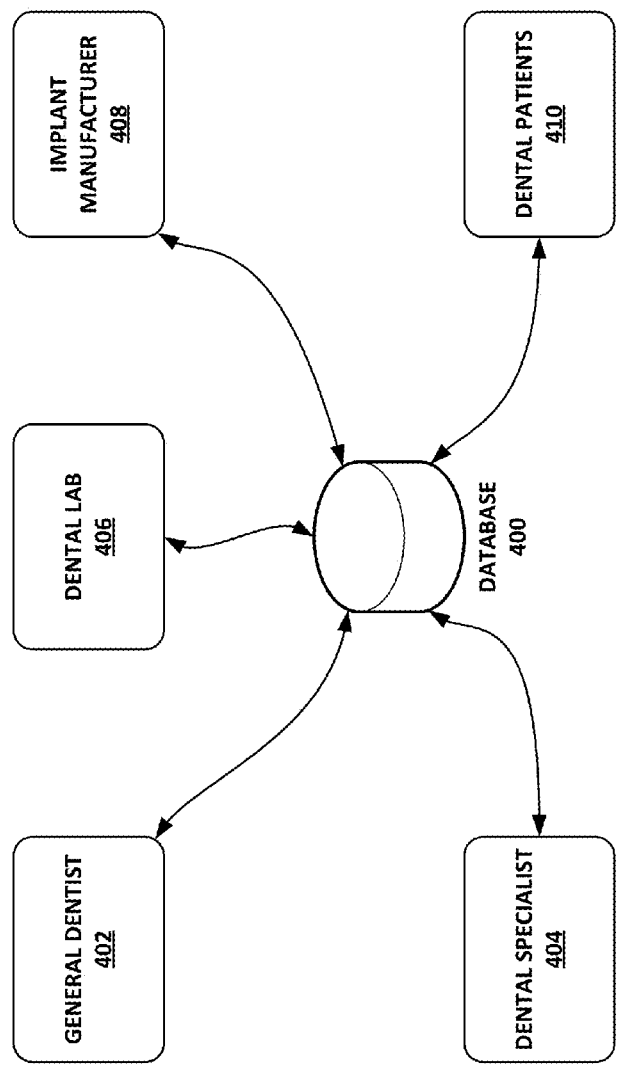
FIG. 4 is a depiction of entities involved in the supply and installation of dental implants, according to an example embodiment.

FIG. 4 depicts a high-level architecture according to example embodiments. The entities in FIG. 4 share access to database 400. Database 400 may be an instance of server data cluster 304 or cluster data storage 308, for example. Database 400 may contain at least three distinct types of information, which may be combined in a single physical or logical database, or divided amongst two or more physical or logical databases. These types of information may be viewable via a computing device on a common set of user interfaces, or may be viewable via different computing devices or via different user interfaces. The user interfaces may be database-driven, web-based interfaces, interfaces that are standalone applications, or other types of interfaces.

The first type of information is dental patient planning and scheduling information. This information allows scheduling coordination between general dentist 402, dental specialist 404, and dental patients 410. Dental lab 406 and implant manufacturers 408 may use or be involved with this information as well.

The second type of information includes records for dental patients 410. These records may track the type of dental implants used on dental patients 410, the details regarding the specific components of the dental implants, as well as information that identifies the general dentist and/or dental specialist who performed the dental implant procedures, and the dates upon which these procedures were performed.

The third type of information is dental implant efficacy information. This information tracks dental implant success and/or failure rates by implant manufacturer, part number, and tooth number across multiple dental patients. In some cases, the failure rate may be affected by other procedures that may be performed before or along with dental implant placement, such as bone graft material, bio-membranes, or Plasma Rich Protein. These procedures are used in more complicated dental implant cases where there is usually less bone or poor bone quality. Further, underlying dental patient medical conditions may impact dental implant efficacy, such as uncontrolled diabetes or use of tobacco products. These other procedures or medical conditions may be tracked as well so that the failure rate of specific types of dental implants reflects these possibly contributory causes.

Regardless, from a large enough number of entries (e.g., a few dozen or few hundred per a specific type of dental implant component) statistically significant conclusions can be drawn regarding the efficacy of the dental implant components. For example, a first model of dental implant may exhibit 10 failures per 100 dental patients, while a second model of dental implant may exhibit only 2 failures per 100 dental patients.

The information in database 400 will be defined in more detail below. Regardless of its form, this information may encompass dozens, hundreds, or even millions of individual dental patient records. Database 400, which may include a computerized database as well as other computing and networking elements, can serve this information over a packet-switched network, for example, to any registered user worldwide. As an example, general dentist 402, dental specialist 404, dental lab 406, implant manufacturer 408, and dental patients 410 may each have unique userid and password combinations to access the information. In addition to the types of dental professionals noted above, other types of doctors or medical personnel may have access to database 400.

However, each of these parties may be provided a different level of access to the information in database 400. General dentist 402 and dental specialist 404 might only be able to access information related to their own dental patients. Dental lab 406 and implant manufacturer 408 might only be able to access information related to orders placed by general dentist 402 and dental specialist 404. Dental patients 410 might only be able to access information related to their own dental history, as well as upcoming appointments. Dental implant efficacy information may be available to some or all parties.

With respect to these parties, database 400 may serve multiple general dentists, dental specialists, dental labs, implant manufacturers, and dental patients. In some cases, database 400 may be a centralized or distributed database serving dozens, hundreds, thousands, or even millions of individual users.

Further, database 400 may include or be integrated with the inventory software used by any of these parties. For instance, when a dental implant restoration procedure is scheduled with general dentist 402, the availability of the dental implant components to be used therewith may be checked against the inventory of general dentist 402. Any components not in the inventory may be added, perhaps automatically, to a purchase order. If the components are needed immediately, a special purchase order may be prepared, again perhaps automatically, for the immediate or timely ordering of these components. Further, information regarding any dental implant components ordered for a particular dental patient may be placed in that dental patient's dental history in database 400.

Additionally, when ordering dental implant components or any office or professional supplies, general dentist 402 and/or dental specialist 404 may use a scanner or image capture device to obtain a digital representation of each item. This digital representation may be, for instance, a number or a bar code. In some cases, the associated items may be automatically added to an online shopping cart (manual entry is also possible) or added to a list of items to order later. Based on when the items are needed, an online purchase may occur immediately, or at some point in the future. Further, a digital representation of a particular item may link to a web site of a manufacturer of that component, so that the user can view information regarding the item.

General dentist 402 may be an entity that provides maintenance and oral hygiene of a dental patient's teeth. These services may include examination, tooth cleaning, x-rays, and restorative dentistry to repair the effects of tooth decay and gum disease. With respect to dental implants, general dentist 402 may recommend dental implant surgery to dental patients 410, obtain surgical guides for such surgery, perform dental implant surgery, as well as undertake the placement of a dental implant restoration (e.g., a crown or prosthesis) after surgery.

Dental specialist 404 may be an oral surgeon, periodontist, endodontist, prosthodontist, orthodontist, or another type of dental professional. As such, dental specialist 404 may extract teeth, as well as diagnose and treat various types of oral and maxillofacial diseases, injuries and defects. With respect to dental implants, dental specialist 404 may extract any remaining parts of the tooth to be replaced, such as the root. Then the dental implant may be inserted. A dental patient may have one or more follow-up appointments with dental specialist 404 to ensure that the dental implant is integrating properly with the dental patient's jaw, and to take measures if it is not. In some cases, an orthodontist may assess the amount of space needed for dental implant placement in patients undergoing orthodontic treatment. The orthodontist may also request dental implant placement from an oral surgeon to serve as anchorage to enable the movement of teeth.

Dental lab 406 may undertake the manufacturing of crowns, abutments, surgical guides, scan guides, and various dental implant prostheses, among other items related to dental implants. These items may be ordered by general dentist 402 and/or dental specialist 404, and may be shaped precisely for use with a particular dental patient. Dental lab 406 may receive these orders offline or online, and may provide a manufacturing and/or delivery schedule via database 400. For instance, when general dentist 402 orders a crown for a dental patient, the order may be entered into database 400. Dental lab 406 may receive a notification of this order, and schedule the crown for manufacturing. This schedule may be made available, via database 400, to general dentist 402 and/or dental specialist 404 for example. Dental lab 406 may update the schedule when the crown is available, and when it is shipped.

In some cases, dental lab 406 may maintain records of the type of metals used in, other properties of, and/or recommended procedures, for various dental implant components. This information may also be provided to database 400, and may be incorporated into the dental histories of dental patients on a tooth by tooth basis. Thus, if a general dentist or dental specialist repairs a particular dental implant, the proper tools and procedures can be determined.

In some embodiments, a warning may be displayed in the schedule of general dentist 402, or otherwise communicated to general dentist 402, a certain number of hours (e.g., 24 or 48) in advance if the dental patient's procedure depends on delivery of a certain dental implant component, but the component was not yet received from dental lab 406. This would help avoid a dental patient coming for an appointment only to find that the general dentist 402 cannot yet perform the scheduled procedure.

Implant manufacturer 408 may be a company that provides dental implant components. For instance, implant manufacturer 408 may make various types of dental components, including dental implants, and may identify each with a model or part number. Each dental implant component may be associated with other ancillary dental implant components and/or tools. For instance, a particular dental implant model may have a particular part number, and may be designed to be work with a limited number of abutments, and screws of a certain size. The screws may require use of a particular type of screwdriver or torque wrench for placement. These dependencies and relationships may be represented in database 400 so that they are clear to general dentist 402 and/or dental specialist 404.

Dental patients 410 may be any number of individual dental patients. In some cases, a dental patient may have dental implants, and in other cases a dental patient might not. As noted above, any of dental patients 410 may access their own (or perhaps their family's) dental information via database 400. In some cases, dental patients 410 may be required to authorize release of this information before it is entered into database 400.

FIG. 4 is an example, logical diagram. While general dentist 402, dental specialist 404, dental lab 406, implant manufacturer 408, and dental patients 410 may communicate and share information via database 400, these entities may communicate through other means, such as telephone, postal mail, email, online ordering, and so on. Such communication may be tracked, in various ways, through database 400.

4. EXAMPLE DENTAL IMPLANT COMPONENTS

Figure 5A:
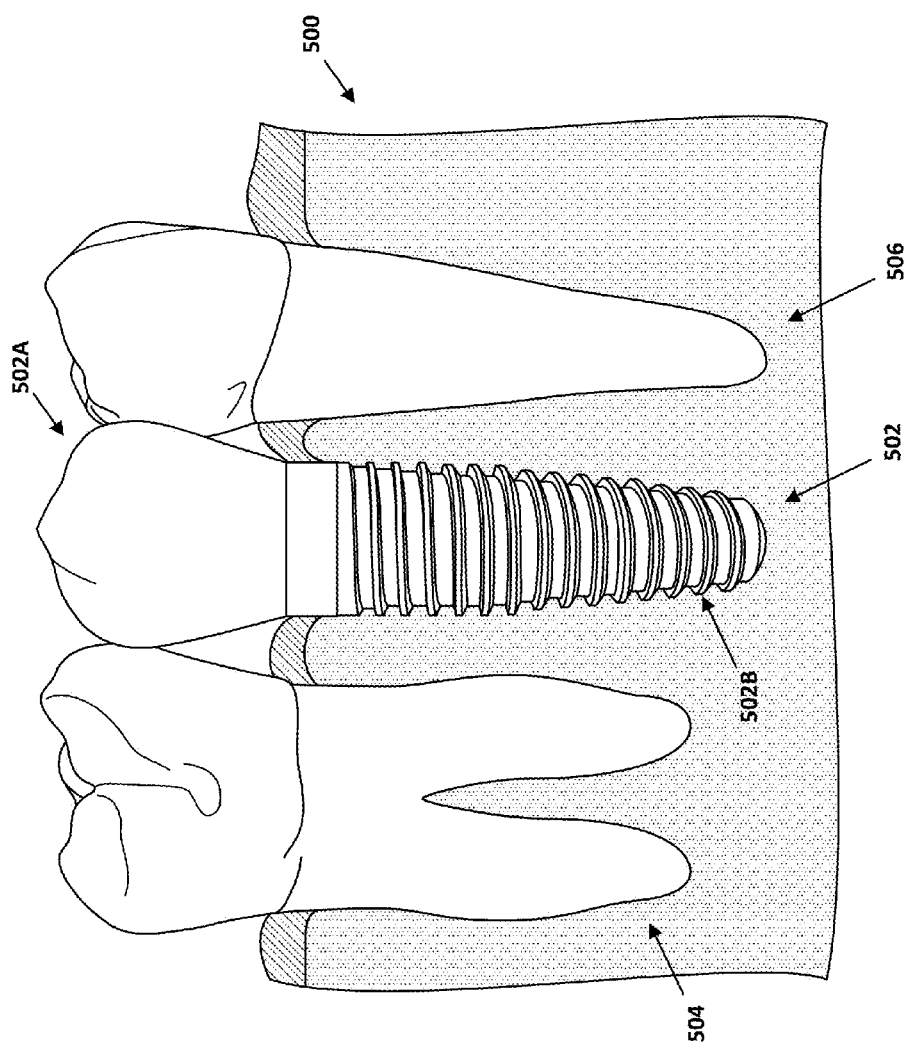
FIG. 5A depicts a dental implant between two natural teeth in a gum-line, according to an example embodiment.

FIG. 5A depicts teeth in a gum-line 500, according to an example embodiment. Tooth 502 is a dental implant, while tooth 504 and tooth 506 are natural teeth. Tooth 502 includes crown 502A, which may be designed to match the shape, color, and bite characteristics of a dental patient's natural teeth. Tooth 502 also includes dental implant 502B, which is screwed into the dental patient's gums and jaw.

Figure 5B:
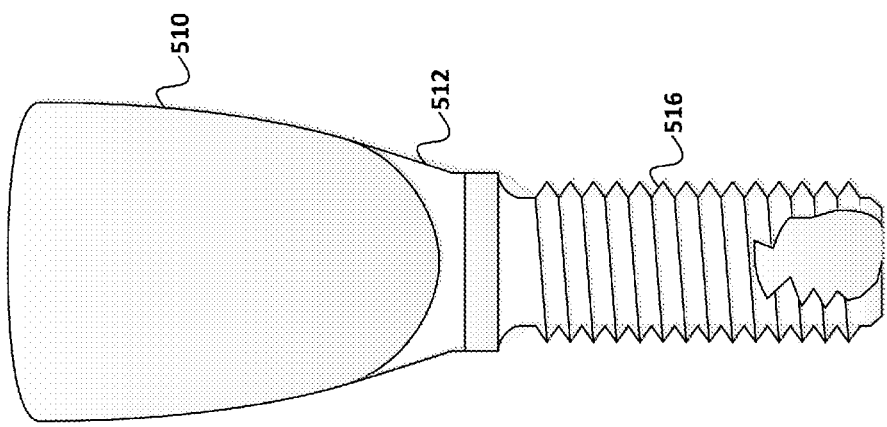
FIG. 5B depicts parts of a dental implant, according to an example embodiment.
Figure 5B:
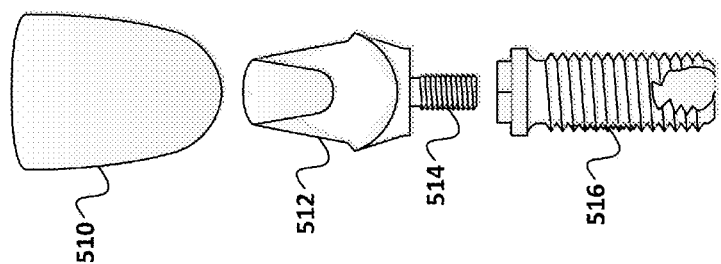

FIG. 5B depicts the parts of an artificial tooth, along with the artificial tooth as fully assembled. The artificial tooth includes crown 510, abutment 512, abutment screw 514 and dental implant 516. Crown 510 is the part of the artificial tooth that projects from the gum. Crowns may be hand-made or machined according to specific requirements. Porcelains or metals may be used to construct a crown. Abutment 512 is a junction between crown 510 and dental implant 516. The rotation of abutment 512 may be controlled via lugs shaped on the stem of the abutment, which restrict this rotation to particular incremental steps. Different dental implant manufacturers may use different lug systems with more or fewer steps. Abutment 512 may be shaped so that it can be placed at an angle to dental implant 516, and may be custom designed in some cases. Typically, abutment 512 is screwed into dental implant 516 using, for example, a screwdriver or torque wrench.

Dental implant 516 provides an anchor or foundation for crown 510. It may be screwed into the bone of the dental patient's jaw, and may provide a fixed platform on which abutment 512 can be attached. Bone tissue can grow around dental implant 516, regenerating and strengthening the jaw, and reducing the bone loss which occurs when natural teeth are removed. Dental implant 516 may be made in various lengths, widths, and shapes. Different dental implant manufacturers may provide different dental implant designs that have various features.

Not shown in FIGS. 5A and 5B are surgical guides and impression copings. Surgical guides are drilling templates that define a preferred location of a dental implant with respect to the dental patient's other teeth. A general dentist may provide a surgical guide to a dental specialist, so that the dental specialist can place the dental implant in a position that allows for proper restoration of the tooth. A surgical guide can reduce surgery time, improve the accuracy of dental implant placement, reduce the need for angle-changing abutments, and improve the aesthetic value of the restoration. There are a variety of surgical guide types, ranging in sophistication and cost from inexpensive vacuum-form shells to cone beam computed tomography and computer-derived templates.

An impression coping is an imprint or negative likeness of the dental patients teeth and gum-line as they relate to the dental implant position in the jaw. Impression copings are typically made after dental implant surgery, but before abutments and crowns are placed. Impression copings assist a general dentist in determining the alignment of the dental implants with respect to the rest of the dental patient's teeth. With this information, the general dentist can determine proper abutment angles and crown shapes. Impression copings are typically made with impression material to capture the relationship of the dental implant to the surrounding bone, teeth, and soft tissue so that a crown or prosthesis can be made. Thus, the impression process may use a substance (such as a polyvinyl material) that becomes relatively hard or set while in contact with the dental patient's teeth, gum-line, and impression coping. From an impression coping, a positive cast of the dental patient's teeth and gum-line can be formed. Impressions can also be taken digitally and transmitted to a dental lab for fabrication of dental implant restorative components.

5. EXAMPLE INTERFACES AND PROCEDURES

FIG. 6A depicts example dashboard view 600. This view provides a general dentist and/or a dental specialist with a way of rapidly determining the status of one or more dental patients who are considering, scheduled for, or recovering from dental implant surgery and follow-up procedures. In FIG. 6A, dashboard view 600 is for a general dentist, Jane A. Doe. Dashboard views for dental specialists may resemble that of FIG. 6A.

Calendar 602 allows the user to select a particular date and view all events associated with that date. These events may be, for instance, appointments, phone calls, indications of when each dental implant component is to be ordered, has been ordered, is to be received, or has been received, and so on. Selecting a date may result in a daily (e.g., hour-by-hour) interface view being displayed, which is not shown herein. According to calendar 602, the current date is Jul. 1, 2015. Warnings may appear on the schedule if a dental patient is due for treatment the next day or two days and a dental implant component is not available in stock or is not scheduled to be received from the manufacturer or dental lab within that time frame.

Column headings 604 may indicate that there are at least three columns in this part of dashboard view 600. These columns may include, for example, dental patient names, the latest event related that that dental patient that has occurred, and the next upcoming event related to that dental patient that is scheduled to occur.

To that end, entry 606 for dental patient Alice Smith, indicates that on Jun. 27, 2015, a schedule entry was created for the dental patient's dental implant surgery, and that this surgery is scheduled to take place on Jul. 8, 2015. Entry 608, for dental patient Robert Jones, indicates that dental implant surgery was conducted on Jun. 29, 2015 with dental specialist Dr. Roberts, and that the dental patient is scheduled for a follow-up appointment with the general dentist on Aug. 15, 2015. Entry, 610 for dental patient Cathy Benton, indicates that dental implants have been ordered from Company A on Jun. 25, 2015, and that abutments are scheduled to arrive on Jul. 7, 2015.

A user can search for a specific dental patient by entering their name into search box 612. A dental patient's first name, last name, or both may be entered. If multiple dental patients with the same name are in the database (e.g., database 400) and associated with the general dentist's practice, each dental patient may be listed under column headings 604.

Figure 6B:
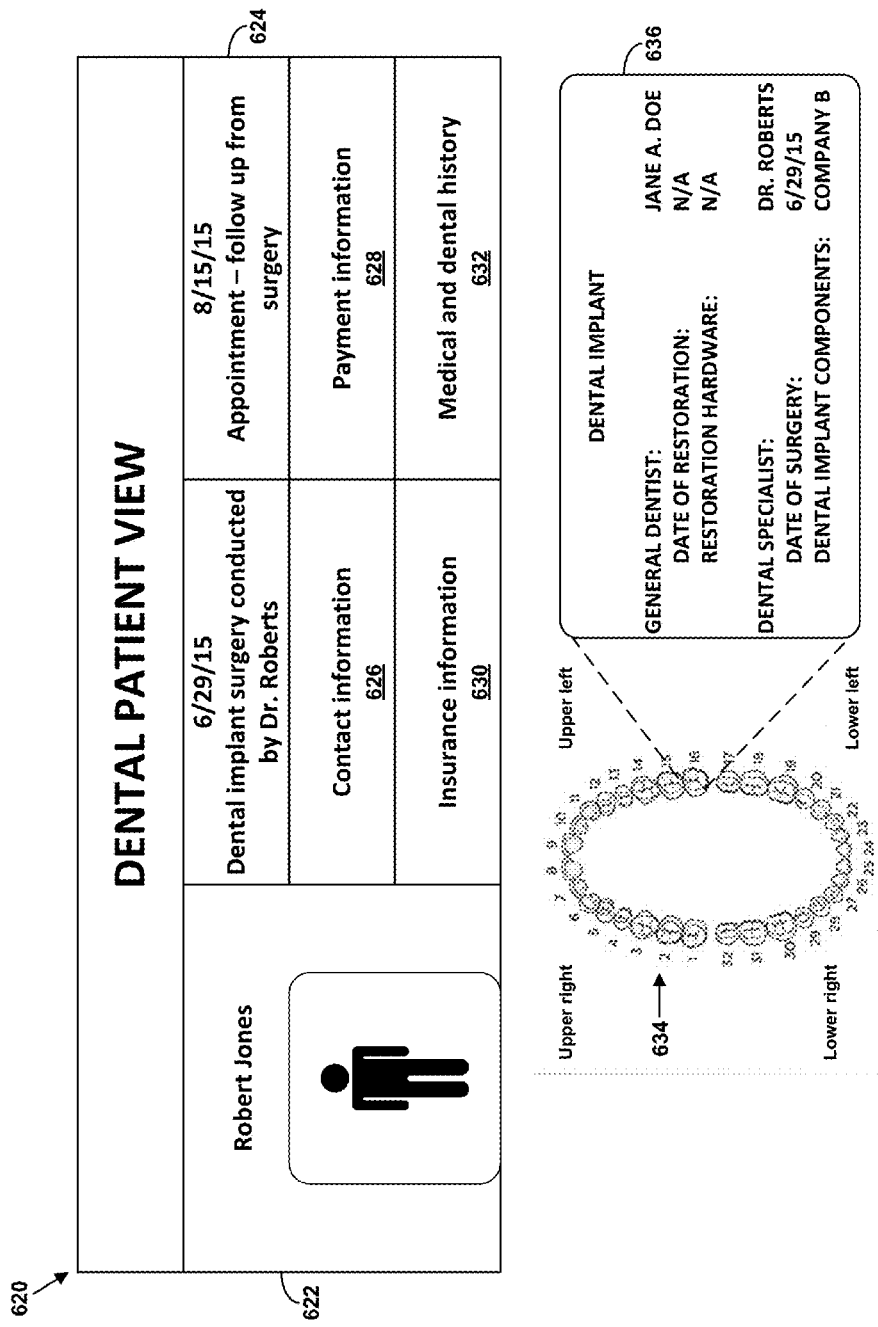
FIG. 6B depicts a dental patient view of a dental patient database, according to an example embodiment.

By selecting a dental patient, for instance from a listing such as the one in FIG. 6A or via a search, dental patient view 620 may be displayed. In this view, depicted in FIG. 6B, information related to a particular dental patient may be arranged.

For instance, dental patient identifying information 622, such as the dental patient's name and/or picture may be included. Further, row 624 may display recent and upcoming events related to the dental patient. Similar to entry 608 of FIG. 6A, information in this row indicates that dental implant surgery was conducted on Jun. 29, 2015 with dental specialist Dr. Roberts, and that the dental patient is scheduled for a follow-up appointment with the general dentist on Aug. 15, 2015.

Dental patient view 620 may also include other information regarding the dental patient, such as contact information 626, payment information 628, insurance information 630, and/or medical and dental history 632. Contact information 626 may include phone numbers, email addresses, and/or physical addresses at which the dental patient can be contacted. Payment information 628 may include records of the dental patient's bills and payments including any outstanding balances, as well as credit card information, for instance. Insurance information 630 may include names of the dental patient's insurance carriers, policy numbers, and/or group numbers. Medical and dental history 632 may include relevant dates, surgical procedures, other procedures, and notes regarding the dental patient's health. For instance, dental patients with diabetes, or who are tobacco users, may be flagged or emphasized in dental patient view 620, as these health issues may negatively impact dental implant integration.

In some cases, medical and dental history 632 may contain information specifying whether the dental patient is diabetic and/or a tobacco user. If the dental patient is diabetic, medical and dental history 632 may indicate further whether the dental patient has his or her diabetes under control (e.g., maintaining blood sugar levels below a threshold concentration). If the dental patient is a tobacco user, medical and dental history 632 may indicate further whether the dental patient is a light user (e.g., less than 1 pack per day), moderate user (e.g., 1-2 packs per day), or a heavy user (e.g., more than 2 packs per day).

Medical and dental history 632 may also include information regarding the dental patient's prescriptions and preferred pharmacy. Thus, when a general dentist or dental specialist prescribes a medication for the dental patient, this information can be entered into medical and dental history 632, and the prescription may automatically be sent to the preferred pharmacy.

Additionally, dental patient view 620 may include a representation 634 of the dental patient's teeth. These teeth may be numbered from 1 to 32 starting with the upper right third molar, continuing to the upper left third molar, then down to the lower left third molar, and to the lower right third molar. If a user clicks on, hovers a pointer over, or otherwise selects a specific tooth in representation 634, tooth-level detail 636 may be displayed. This detail may include one or more x-rays or cone beam computed tomography scans of the tooth, whether the tooth is natural or artificial, any procedures that have been performed on the tooth, and/or notes regarding treatment or follow-up care for the tooth. For example, tooth-level detail 636 for tooth 16 in FIG. 6B indicates that this tooth includes a dental implant, the general dentist involved in the dental implant procedure, that the crown is not yet in place, the dental specialist involved in the dental implant procedures, the date of dental implant placement, and the dental implant components used.

If a particular tooth location has had more than one dental implant procedure, this may be indicated in tooth-level detail 636. For instance, suppose that tooth 16 was initially replaced with a first dental implant, that dental implant failed, and the failed dental implant was subsequently replaced by a second dental implant. In this case, information regarding the first and second dental implants may be present.

For a tooth with a dental implant, dental patient view 620 (or various other views or graphical user interfaces) may provide an option for the user to request identification of the dental implant. For instance, the user might be able to click on a button labeled "ID Implant." In response to clicking on such a button, all known information about the dental implant may be transmitted to a third party for review. This information may include, but is not limited to, an x-ray of the dental implant, any known components therein, whether the implant holds a crown or a prosthesis, and a history of the patient's tooth number associated with the dental implant (e.g., any procedure performed thereto, and when these procedures were performed). The third party may manually or automatically attempt to identify the dental implant components by manufacturer or part number. If this identification is successful, the identifying information may be provided to the user.

From either dashboard view 600 or dental patient view 620, the user may be given the option to select dental implant efficacy view 640. Shown in FIG. 6C, this view allows the user to rapidly determine the efficacy (e.g., failure rate) of a particular dental implant part. For instance, a number of dental implant parts can be displayed, and then sorted using dental implant part type selector 642, manufacturer selector 644, dental specialist selector 646, and/or date of surgery selector 648. Other sorting selectors, such as dental implant modality (e.g., grafts, bio-membranes, Plasma Rich Protein etc.), whether an immediate load process was used or if the dental patient's jaw was given time to heal before the crown or prosthesis was placed, dental patient medical conditions (e.g., diabetes, tobacco use), number of years or experience of dental implant procedures performed by the dental specialist, and so on may be included.

Results 650 may include a list of dental implant parts, associated implant manufacturers, and/or a measured failure rate. Column headings 652 may specify the dental implant part number, manufacturer, and associated failure rate, for example. As indicated by part type selector 642, manufacturer selector 644, dental specialist selector 646, and date of surgery selector 648, only dental implants from Company A, placed by any dental specialist from Jan. 1, 2000 until present day are shown. Notably, this information, as displayed in entries 654, 656, 658, and 660, indicates that part number VZW100 has the highest failure rate (10%), while part number VZW300 has the lowest failure rate (2%). Other part numbers have failure rates between these two extremes.

Dental implants may also be listed by tooth number, and statistics may be compiled using that information because position of the dental implant in the jaw may affect dental implant success (e.g., expected mandibular success can be greater than expected maxillary success for dental implants). A subcategory may specify whether the dental implant had bone graft material, a bio-membrane, or Plasma Rich Protein used. As noted above, the failure rates may incorporate, reflect, or be based on other procedures or medical conditions of dental patients. In some embodiments, the failure rates may ignore failure in dental patients who suffered from poor bone quality, diabetes, or were tobacco users. Alternatively, these factors may be incorporated into the failure rating in some fashion, for instance a dental implant failure in a diabetic patient may be given half the weight as a dental implant failure in a non-diabetic patient. In some cases, dental implant failure rates may be calculated separately for dental patients with diabetes or who use tobacco. These failure rates might be further subdivided based whether the dental patients with diabetes have their diabetes under control, and/or whether the dental patients who use tobacco are light, moderate, or heavy users. Other factors that may influence failure rates include use of bio-membranes, bone graft material, or Plasma Rich Protein.

With respect to dental implant efficacy view 640, one or more of these additional factors may be displayed in results 650, and/or results 650 may be sortable by such factors. In some embodiments, dental specialist selector 646 may be further subdivided to indicate the type of dental professional (general dentist, oral surgeon, periodontist, endodontist, orthodontist, etc.) who performed the procedure. Thus, failure rates may also be displayed by type of dental professional.

The information displayed in dental implant efficacy view 640 may be automatically generated based on dental histories. For instance, if a dental patient receives a dental implant, but this dental implant is replaced within a threshold number of months, e.g., 6, 12, 24, or 48, the dental implant procedure may be considered a failure. On the other hand, a dental implant that is not replaced may be considered a success.

Any of the information displayed in dental implant efficacy view 640, or used to generate the information displayed therein, may be accessible general dentists, dental specialists, dental labs, implant manufacturers, and/or dental patients.

The example computer-implemented interfaces shown in FIGS. 6A, 6B, and 6C are presented for purposes of illustration. Different information may be displayed in these interfaces, and users may be able to navigate between the interfaces in various ways. Additional interfaces may also be available with respective functions. At least one advantage of the example interfaces shown in FIGS. 6A, 6B, and 6C is that dental patient information, including dental histories, can be found in a single location, such as database 400. Preferably, database 400 is not limited to any particular dental practice, so information regarding a large number of dental patients may be shared between dental practices in any geographic locations.

Figure 7A:
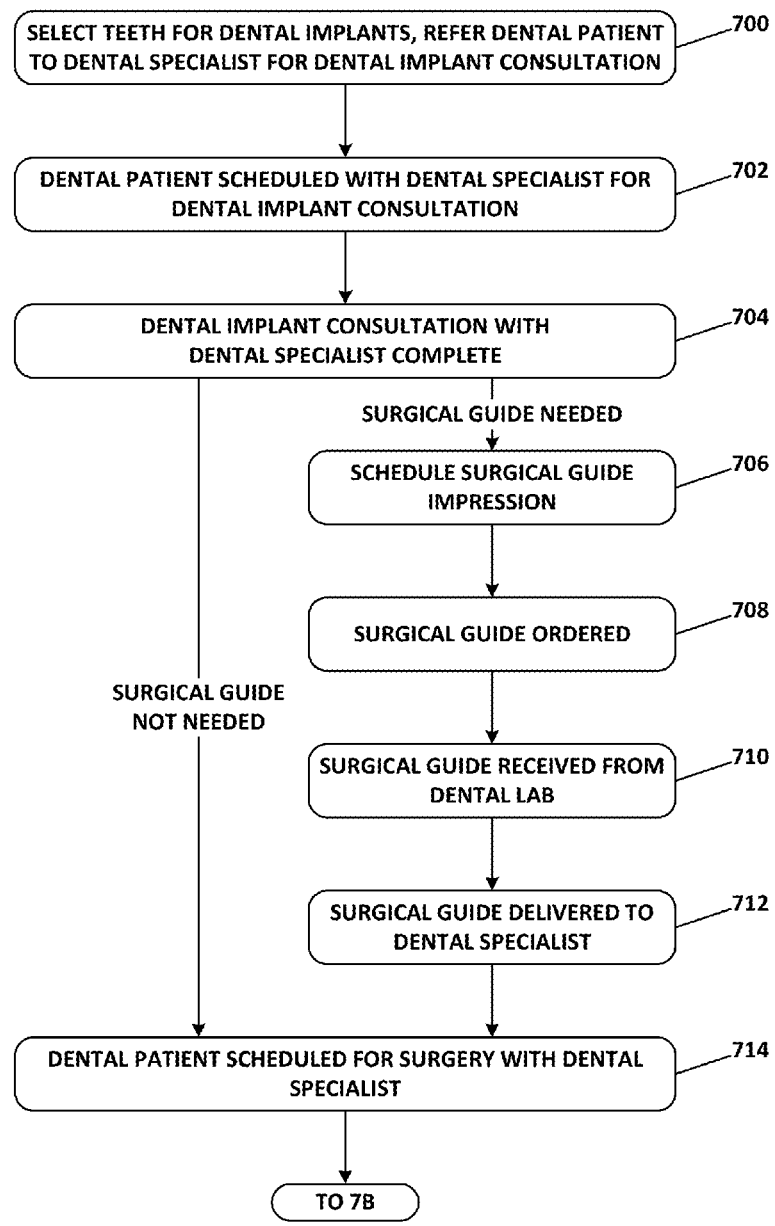
FIG. 7A is a partial flow chart of a general dentist's workflow, according to an example embodiment.
Figure 7B:
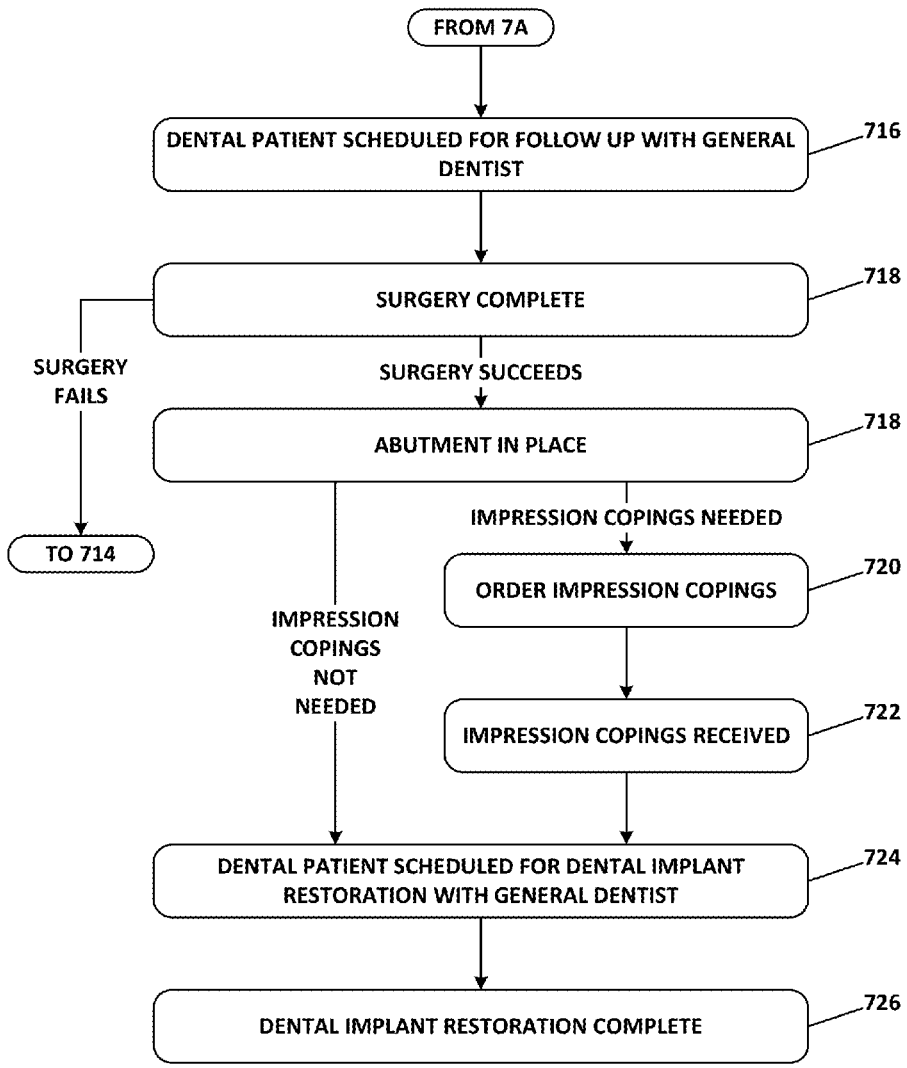
FIG. 7B is another partial flow chart of a general dentist's workflow, according to an example embodiment.
Figure 8:
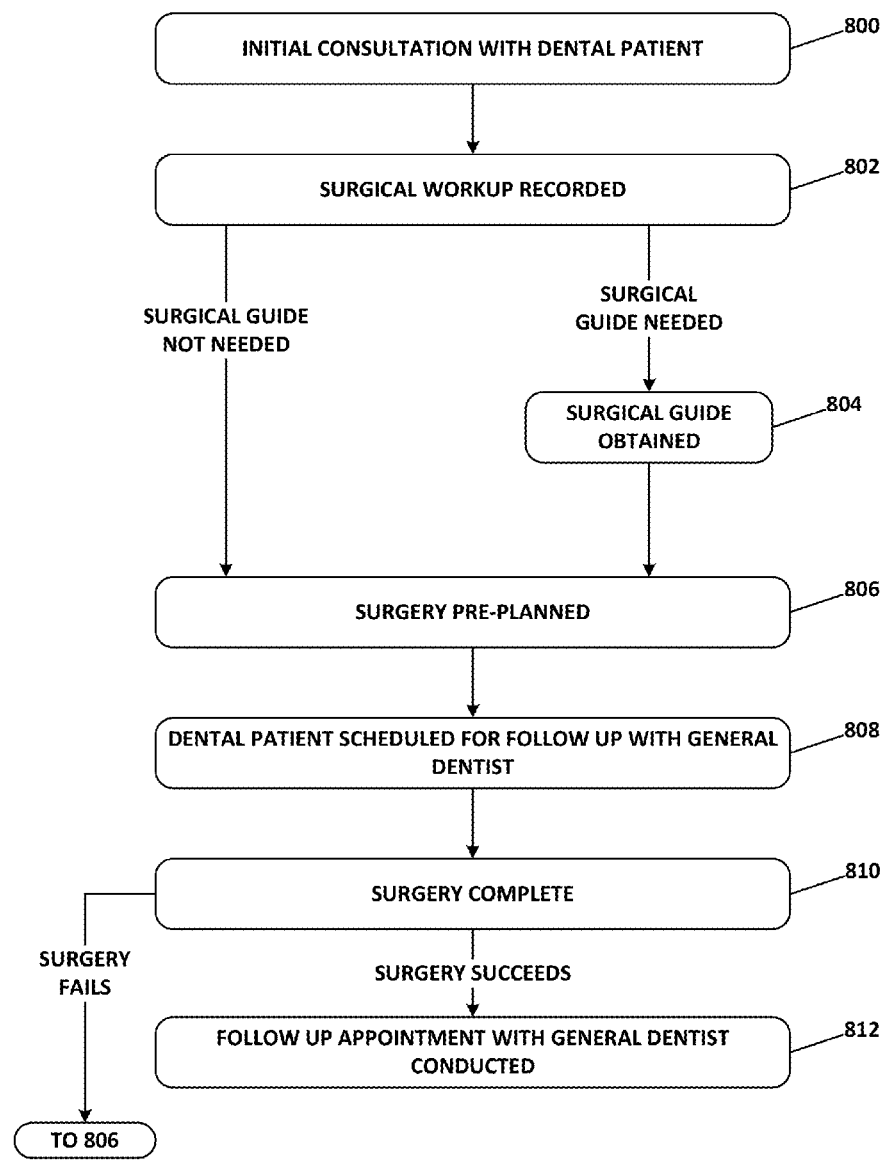
FIG. 8 is a flow chart of a dental specialist's workflow, according to an example embodiment.

FIGS. 7A and 7B depict a flow chart related to procedures that a general dentist may carry out with regard to placement of dental implants and the associated restoration for a dental patient. FIG. 8 depicts a flow chart related to procedures that a dental specialist may carry out with regarding the same dental patient. These flow charts illustrate the coordination and interactions between these dental professionals, dental labs, and implant manufacturers. Each block in any of these figures may include steps where information is retrieved from database 400 and/or written to database 400. Thus, in order to carry out the procedures of these figures, one or more users may access the information in database 400 via one or more computer interfaces, such as web-based interfaces or standalone application interfaces.

Further, the status of any item ordered from a dental lab, implant manufacturer, or other provider or vendor may be tracked in database 400. Thus, for instance, if a surgical guide is ordered from a dental lab, the status of this order may be included in database 400 and updated as needed.

At block 700, the general dentist may select one or more teeth for dental implants, and refer the dental patient to a dental specialist (e.g., an oral surgeon, periodontist, endodontist, prosthodontist, orthodontist, or another type of dental professional) for a dental implant consultation. This referral may be made based on the general dentist's routine examination of the dental patient, or an examination resulting from the dental patient experiencing pain and/or discomfort.

At block 702, the dental patient has been scheduled with the dental specialist for dental implant consultation. This information may be shared between the general dentist and the dental specialist so that both can track the progress of the dental patient. This information may also be automatically integrated into these parties' scheduling software. In some cases, the dental patient may begin the dental implant process by initially consulting with the dental specialist, then being referred to a general dentist.

At block 704, the dental implant consultation with the dental specialist is complete. If the dental patient chooses to not undergo dental implant surgery, the dental patient's dental records will indicate as such and the operations of the flow chart end. Otherwise, the general dentist and/or dental specialist determine whether a surgical guide is needed, and this information will be stored for the general dentist, dental specialist, and/or other parties to access.

If a surgical guide is not needed, blocks 706, 708, 710, and 712 can be skipped. If a surgical guide is needed, then at block 706 the dental patient is scheduled for surgical guide impression. At block 708, after the impression is taken, the surgical guide is ordered from the dental lab. At block 710, the surgical guide is received from the dental lab. At block 712, the surgical guide may be provided to the dental specialist for use during surgery. In some cases the general dentist may receive the surgical guide, confirm that it was properly made, and then provide it to the dental specialist. This information may be stored in database 400 so that the general dentist and dental specialist both are aware of the readiness of the surgical guide.

Regardless, at block 714 the dental patient may be scheduled for surgery with the dental specialist. Turning to FIG. 7B, at block 716, possibly before surgery occurs, the dental patient is scheduled for a follow-up appointment with the general dentist. At block 718, surgery is complete. Information regarding the manufacturer and part number of the dental implant may be entered into database 400 so that it is available to the general dentist. With this information, the general dentist may be able to order dental implant components for restoration of the dental implant.

If surgery fails, the process returns to block 714 for another attempt. If the surgery succeeds, at block 718 an abutment is placed. If impression copings are not needed, blocks 720 and 722 may be skipped. If impression copings are needed, they may be ordered at block 720, and received at block 722. This information may be stored in database 400 so that the general dentist is aware of the readiness of the impression copings and the information about the impression copings used is stored in the patient's dental records.

At block 724, the dental patient may be scheduled for dental implant restoration (e.g., placement of a crown) with the general dentist. At block 726, dental implant restoration may be completed.

Note that at one or more points in FIGS. 7A and 7B there may be an option (not shown) for dental implants to be ordered from an implant manufacturer or inventory checked before the dental patient goes for surgery. Doing so reduces the likelihood that the patient arrives for surgery but the dental implant components are not available. Additionally, a cone beam computed tomography scan may be ordered before or after the dental patient consults with the dental specialist (also not shown). If the scan is to be conducted, a barium guide may be fabricated before the scan takes place. Moreover, warnings may be displayed in any dental patient's schedule if the patient is scheduled for a procedure that takes place within a period of time (e.g., 24 or 48 hours prior) and one or more dental implant components needed for the procedure are not yet on hand.

FIG. 8 depicts the same process as FIGS. 7A and 7B, but from the dental specialist's point of view. As noted above, some general dentists place dental implants, and thus take on the role of a dental specialist. In these cases, the operations of FIGS. 7A, 7B, and 8 may be performed by the same dental professional or practice, perhaps in a more simplified fashion.

Regardless, at block 800 the dental specialist conducts an initial consultation with the dental patient. At block 802, a surgical workup is recorded based on this initial consultation. If a surgical guide is needed, it is obtained from the general dentist at block 804.

At block 806, surgery pre-planning takes place. If any dental implant component needs to be ordered, this is done and surgery is scheduled to take place after the dental implant component is expected to arrive. At block 808, prior to surgery, the dental patient is scheduled for follow-up with the general dentist. At block 810, surgery is complete. If surgery fails, the process returns to block 806. Otherwise, at block 812, the follow-up appointment with the general dentist is conducted.

FIGS. 7A, 7B, and 8 are for purposes of example, and illustrate just some possible embodiments. Other embodiments may be employed, some of which may contain more or fewer blocks, and/or may involve the blocks being organized in a different ordering. Further, as noted above, each block in these figures may involve reading data from and/or writing data to database 400. Additionally, parties involved in the transaction may access the information via database 400 at any time.

6. EXAMPLE OPERATIONS

Figure 9:
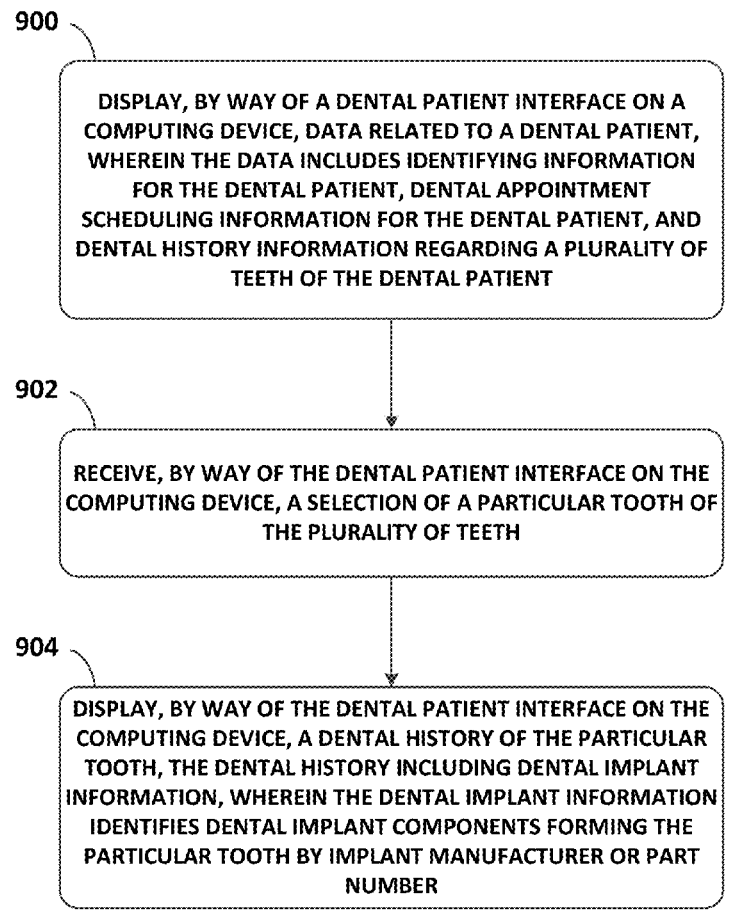
FIG. 9 depicts a flow chart, according to an example embodiment.
Figure 10:
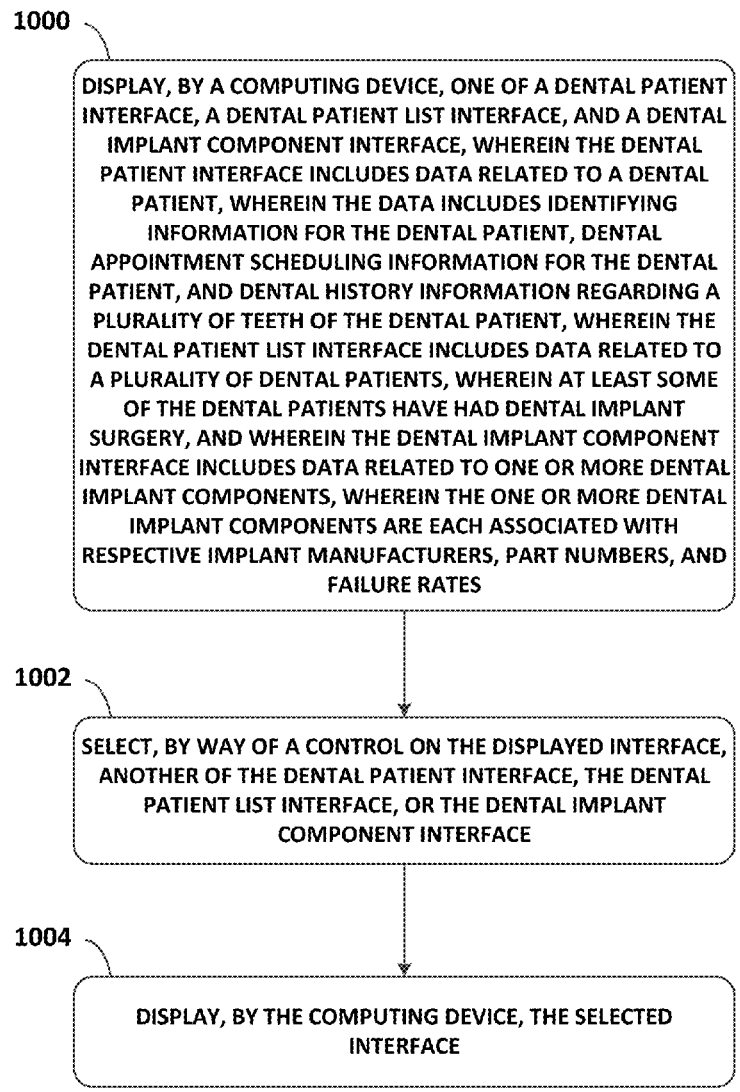
FIG. 10 depicts another flow chart, according to an example embodiment.

FIGS. 9 and 10 are flow charts illustrating example embodiments. The operations illustrated these figures may be carried out by a computing device, such as computing device 200, and/or a cluster of computing devices, such as server cluster 304. However, the operations can be carried out by other types of devices or device subsystems. For example, the operations could be carried out by a portable computer, such as a laptop, smartphone, or a tablet device.

Both of these flow charts may involve computer-implemented user interfaces displaying unique arrangements of information so that one or more parties can rapidly and conveniently have access to the information. In particular, the information may be related to dozens, hundreds, thousands, or more dental patients that are in geographically disparate regions, and visit geographically disparate dental practices.

In both FIGS. 9 and 10, the term "displaying" may be interpreted as "providing for display." Thus, a computing device that "displays" information on a particular interface (e.g., a graphical user interface) may be a server or database device providing this information via a packet-switched network to a client device, for display on the client device. On the other hand, the "displaying" may take place on such client device, and the content displayed may be based on information received from a server or database device. Other possibilities exist.

Block 900 of FIG. 9 may involve displaying, by way of a dental patient interface on a computing device, data related to a dental patient. The data may include identifying information for the dental patient, dental appointment scheduling information for the dental patient, and dental history information regarding a plurality of teeth of the dental patient.

Block 902 may involve receiving, by way of the dental patient interface on the computing device, a selection of a particular tooth of the plurality of teeth. In some cases, the tooth may be a prosthesis.

Block 904 may involve, possibly in response to the selection of the particular tooth, displaying, by way of the dental patient interface on the computing device, a dental history of the particular tooth. The dental history may include dental implant information that identifies dental implant components forming the particular tooth by implant manufacturer or part number.

In some embodiments, the dental implant information may also identify respective dates on which each dental implant component was placed in the dental patient. Further, the dental implant information may also identify respective dental professionals who placed each dental implant component in the dental patient. The respective dental professionals may include at least two different dental professionals associated with at least two different dental practices.

Some embodiments may involve receiving, by way of the dental patient interface on the computing device, a second selection of a second particular tooth of the plurality of teeth. Possibly in response to the second selection of the second particular tooth, the embodiments may include displaying, by way of the dental patient interface on the computing device, a second dental history of the second particular tooth. The second dental history may include second dental implant information that identifies dental implant components forming the second particular tooth by manufacturer and model.

The dental appointment scheduling information for the dental patient may include dates and times of upcoming appointments for dental implant surgery with dental specialist and follow-up with a general dentist. The dental appointment scheduling information for the dental patient may indicate whether dental implant components for the upcoming appointments have been ordered or are in stock with the dental specialist or general dentist.

Some embodiments may include receiving, by way of the dental patient interface on the computing device, an indication that a dental implant component interface on the computing device has been selected. Possibly in response to selection of the dental implant component interface on the computing device, the embodiments may also involve displaying, by the dental implant component interface on the computing device, a list of one or more dental implant components related to dental implants. The one or more dental implant components may each be associated with respective manufacturers, part numbers, and failure rates. The list may be sortable by implant manufacturer, part number, and failure rate.

Some embodiments may involve receiving, by way of the dental patient interface on the computing device, an indication that a dental patient list interface on the computing device has been selected. Possibly in response to selection of the dental patient list interface on the computing device, the embodiments may also involve displaying, by the dental patient list interface on the computing device, data related to a plurality of dental patients. At least some of the dental patients may have had dental implant surgery.

The dental patient list interface may include data related to at least 20 dental patients who have had dental implant surgery. Dental histories of the at least 20 dental patients may indicate that the at least 20 dental patients have been patients of at least 20 different dental professionals. The dental histories of the at least 20 dental patients may also indicate that the at least 20 dental patients reside in at least 20 different geographical regions. These geographical regions may be disparate, in the sense that they may be distributed throughout a state, province, country, or the world.

However, more or fewer dental patients, dental professionals, or geographical regions may be specified in this fashion. For instance, embodiments may involve 10, 50, 100, 1000, or more dental patients, dental professionals, and/or geographical regions. Particularly, displaying information related to such a large number of dental patients, dental professionals, and/or geographical regions necessitates computer implementation. This patient information may be stored in one or more centralized or distributed databases, and may be gathered from dental practices throughout a state, province, country, or the world. Advantageously, this results in patient's dental histories being available as those patients move from location to location. Regardless, collecting, storing, and displaying this information would not be possible without computer implementation. For instance, dental information on such a large number of items from different dental practices would not be available to geographically dispersed dental professionals otherwise.

Further, the embodiments herein specify how interactions between a user and one or more interfaces on a computing device yield new results. These results involve the users being able to rapidly and efficiently (i) determine the status of dental patients with respect to upcoming or previous dental implant surgeries, (ii) determine the dental history of specific teeth of a dental patient even if that dental history include procedures performed by other dental professionals in other geographic locations, and (iii) determine the efficacy of particular dental implant components based on patients' dental histories. Previously, making these determinations might not have been practical or possible. The interfaces described herein present this information in an intuitive and simple fashion, allowing a dental professional to rapidly make these determinations. Thus, the intersection of the new features of these embodiments and the computer implementation thereof go beyond conventional and routine operations.

As an example, for each tooth of a particular dental patient, a user may be able to select that tooth and the interface may display information regarding the dental history of the tooth. The dental history may include records of dental procedures performed on the tooth, identification of the dental professionals who performed them, and the specific dental implant components and/or procedures used for the tooth. The dental history may extend years into the past, with records of multiple dental professionals performing multiple procedures.

Block 1000 of FIG. 10 may involve displaying, by a computing device, one of a dental patient interface, a dental patient list interface, and a dental implant component interface. The dental patient interface may include data related to a dental patient. This data may include identifying information for the dental patient, dental appointment scheduling information for the dental patient, and dental history information regarding a plurality of teeth of the dental patient. The dental patient list interface may include data related to a plurality of dental patients, where at least some of the dental patients have had dental implant surgery. The dental implant component interface may include data related to one or more dental implant component for dental implants, each associated with respective manufacturers, part numbers, and/or failure rates. In some embodiments, the failure rates may be automatically calculated based on the dental histories of multiple dental patients.

Block 1002 may involve selecting, by way of a control on the displayed interface, another of the dental patient interface, the dental patient list interface, or the dental implant component interface. Block 1004 may involve displaying, by the computing device, the selected interface. The interface controls herein may be any form of button, selector, dial, switch, slider, menu item, data item, or other component that can be selected by a user.

The embodiments of FIG. 10 are non-limiting and may be combined with any embodiment, feature or aspect discussed in conjunction with FIG. 9 or any previous figure.

7. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:
1. A method comprising:
generating, for display on a first portion of a first graphical user interface of a computing device, a dental patient view interface that contains a representation of a plurality of teeth of a dental patient and data related to the dental patient, wherein the data includes identifying information for the dental patient, dental appointment scheduling information for the dental patient, medical history information of the dental patient, and dental history information regarding the plurality of teeth of the dental patient;
transmitting, to the computing device, a representation of the dental patient view interface;
receiving, by way of the dental patient view interface on the computing device, a selection of a particular tooth of the plurality of teeth;
in response to the selection of the particular tooth, generating, for display on a second portion of the first graphical user interface, a tooth-level detail interface that contains a dental history of the particular tooth, the dental history including dental implant information, wherein the dental implant information identifies dental implant components forming the particular tooth by implant manufacturer or part number, respective dates on which each dental implant component was placed in the dental patient, and respective dental professionals who placed each dental implant component in the dental patient;
transmitting, to the computing device, data representing the tooth-level detail interface;
receiving, by way of the dental patient view interface, an indication that a dental implant component interface on the computing device has been selected;

in response to the selection of the dental implant component interface, generating, for display on a second graphical user interface of the computing device, a sortable list of one or more of the dental implant components, wherein the dental implant components in the sortable list are each associated with respective implant manufacturers, part numbers, and failure rates, and wherein the failure rates are calculated based on dental history information of multiple dental patients; and transmitting, to the computing device, data representing the sortable list.

2. The method of claim 1, wherein the respective dental professionals include at least two different dental professionals associated with at least two different dental practices.

3. The method of claim 1, further comprising:
receiving, by way of the dental patient view interface on the computing device, a second selection of a second particular tooth of the plurality of teeth; and
in response to the second selection of the second particular tooth, generating, for display on the second portion of the first graphical user interface, the tooth-level detail interface that contains a second dental history of the second particular tooth, the second dental history including second dental implant information, wherein the second dental implant information identifies dental implant components forming the second particular tooth by manufacturer and model.

4. The method of claim 1, wherein the dental appointment scheduling information for the dental patient includes dates and times of upcoming appointments for dental implant surgery with a dental specialist, and follow-up with a general dentist.

5. The method of claim 4, wherein the dental appointment scheduling information for the dental patient indicates whether dental implant components for the upcoming appointments have been ordered or are in stock with the dental specialist or general dentist.

6. The method of claim 1, wherein the sortable list is sortable by implant manufacturer, part number, and failure rate.

7. The method of claim 1, further comprising:
receiving, by way of the dental patient view interface on the computing device, an indication that a dental patient list interface on the computing device has been selected; and
in response to selection of the dental patient list interface on the computing device, displaying, by the dental patient list interface on the computing device, data related to a plurality of dental patients, wherein at least some of the dental patients have had dental implant surgery.

8. The method of claim 7, wherein the dental patient list interface includes data related to at least 20 dental patients who have had dental implant surgery, wherein dental histories of the at least 20 dental patients indicate that the at least 20 dental patients have been patients of at least 20 different dental professionals.

9. The method of claim 8, wherein the dental histories of the at least 20 dental patients indicate that the at least 20 dental patients reside in at least 20 different geographical regions.

10. An article of manufacture including a non-transitory computer-readable medium, having stored thereon program instructions that, upon execution by a computing device, cause the computing device to perform operations comprising:

generating, for display on a first portion of a first graphical user interface of a client device, a dental patient view interface that contains a representation of a plurality of teeth of a dental patient and data related to the dental patient, wherein the data includes identifying information for the dental patient, dental appointment scheduling information for the dental patient, medical history information of the dental patient, and dental history information regarding the plurality of teeth of the dental patient;

transmitting, to the client device, a representation of the dental patient view interface;

receiving, by way of the dental patient view interface on the client device, a selection of a particular tooth of the plurality of teeth;

in response to the selection of the particular tooth, generating, for display on a second portion of the first graphical user interface, a tooth-level detail interface that contains a dental history of the particular tooth, the dental history including dental implant information, wherein the dental implant information identifies dental implant components forming the particular tooth by implant manufacturer or part number, respective dates on which each dental implant component was placed in the dental patient, and respective dental professionals who placed each dental implant component in the dental patient;

transmitting, to the client device, data representing the tooth-level detail interface;

receiving, by way of the dental patient view interface, an indication that a dental implant component interface on the computing device has been selected;

in response to the selection of the dental implant component interface, generating, for display on a second graphical user interface of the client device, a sortable list of one or more of the dental implant components, wherein the dental implant components in the sortable list are each associated with respective implant manufacturers, part numbers, and failure rates, and wherein the failure rates are calculated based on dental history information of multiple dental patients; and transmitting, to the client device, data representing the sortable list.

11. The article of manufacture of claim 10, wherein the dental appointment scheduling information for the dental patient includes dates and times of upcoming appointments for dental implant surgery with a dental specialist, and follow-up with a general dentist.

12. The article of manufacture of claim 11, wherein the dental appointment scheduling information for the dental patient indicates whether dental implant components for the upcoming appointments have been ordered or are in stock with the dental specialist or general dentist.

13. The article of manufacture of claim 10, the operations further comprising:
receiving, by way of the dental patient view interface on the client device, an indication that a dental patient list interface on the computing device has been selected; and
in response to selection of the dental patient list interface on the client device, displaying, by the dental patient list interface on the computing device, data related to a plurality of dental patients, wherein at least some of the dental patients have had dental implant surgery.

14. The article of manufacture of claim 10, wherein the sortable list is sortable by implant manufacturer, part number, and failure rate.

15. The method of claim 1, wherein the medical history information and the dental history information indicate whether the dental patient is a tobacco user and whether the dental patient is a light tobacco user, moderate tobacco user, or a heavy tobacco user, and wherein the failure rates are calculated based on this information.

16. A computing system comprising:
at least one processor;
memory; and
program instructions, stored in the memory, that upon execution by the at least one processor cause the computing system to perform operations comprising:
generating, for display on a first portion of a first graphical user interface of a computing device, a dental patient view interface that contains a representation of a plurality of teeth of a dental patient and data related to the dental patient, wherein the data includes identifying information for the dental patient, dental appointment scheduling information for the dental patient, medical history information of the dental patient, and dental history information regarding the plurality of teeth of the dental patient;
transmitting, to the computing device, a representation of the dental patient view interface;
receiving, by way of the dental patient view interface on the computing device, a selection of a particular tooth of the plurality of teeth;
in response to the selection of the particular tooth, generating, for display on a second portion of the first graphical user interface, a tooth-level detail interface that contains a dental history of the particular tooth, the dental history including dental implant information, wherein the dental implant information identifies dental implant components forming the particular tooth by implant manufacturer or part number, respective dates on which each dental implant component was placed in the dental patient, and respective dental professionals who placed each dental implant component in the dental patient;
transmitting, to the computing device, data representing the tooth-level detail interface;
receiving, by way of the dental patient view interface, an indication that a dental implant component interface on the computing device has been selected;
in response to the selection of the dental implant component interface, generating, for display on a second graphical user interface of the computing device, a sortable list of one or more of the dental implant components, wherein the dental implant components in the sortable list are each associated with respective implant manufacturers, part numbers, and failure rates, and wherein the failure rates are calculated based on dental history information of multiple dental patients; and
transmitting, to the computing device, data representing the sortable list.

17. The method of claim 1, wherein the dental implant information indicates that at least part of the dental implant components are not yet in place.

18. The method of claim 1, wherein the dental implant information indicates that the particular tooth was initially replaced with a first dental implant, the first dental implant failed, and the first dental implant was subsequently replaced by a second dental implant.

19. The article of manufacture of claim 10, wherein the dental implant information indicates that at least part of the dental implant components are not yet in place.

20. The article of manufacture of claim 10, wherein the dental implant information indicates that the particular tooth was initially replaced with a first dental implant, the first dental implant failed, and the first dental implant was subsequently replaced by a second dental implant.

* * * * *